United States Patent
Okamoto et al.

(10) Patent No.: US 11,401,483 B2
(45) Date of Patent: Aug. 2, 2022

(54) ISOBUTYRIC ESTER COMPOUND HAVING BUTYRYLOXY GROUP OR PIVALOYLOXY GROUP AT α-POSITION AND FRAGRANCE COMPOSITION

(71) Applicant: MITSUBISHI GAS CHEMICAL COMPANY, INC., Chiyoda-ku (JP)

(72) Inventors: Atsushi Okamoto, Niigata (JP); Eriko Kushida, Niigata (JP); Umi Yokobori, Niigata (JP); Kyoko Kimura, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 11 days.

(21) Appl. No.: 17/255,097

(22) PCT Filed: Jun. 26, 2019

(86) PCT No.: PCT/JP2019/025392
§ 371 (c)(1),
(2) Date: Dec. 22, 2020

(87) PCT Pub. No.: WO2020/004464
PCT Pub. Date: Jan. 2, 2020

(65) Prior Publication Data
US 2021/0269741 A1     Sep. 2, 2021

(30) Foreign Application Priority Data

Jun. 26, 2018  (JP) .............................. JP2018-121102
Nov. 28, 2018  (JP) .............................. JP2018-222711

(51) Int. Cl.
C11B 9/00       (2006.01)
C07C 69/34      (2006.01)

(52) U.S. Cl.
CPC ............ *C11B 9/0019* (2013.01); *C07C 69/34* (2013.01); *C11B 9/003* (2013.01); *C07C 2601/02* (2017.05); *C07C 2601/04* (2017.05)

(58) Field of Classification Search
CPC ....... C11B 9/0019; C11B 9/003; C07C 69/34; C07C 2601/02; C07C 2601/04
See application file for complete search history.

(56) References Cited

U.S. PATENT DOCUMENTS

| 3,368,943 A | 2/1968 | Gilbert et al. |
| 3,448,110 A | 6/1969 | Griot et al. |
| 2011/0097291 A1* | 4/2011 | Vial .................. C11B 9/0019 |
| | | 512/26 |
| 2016/0130526 A1 | 5/2016 | Vial |
| 2018/0208540 A1 | 7/2018 | Vial et al. |
| 2018/0320105 A1 | 11/2018 | Vial |
| 2019/0077743 A1 | 3/2019 | Vial et al. |

FOREIGN PATENT DOCUMENTS

| JP | 54-92635 A | 7/1979 |
| JP | 2011-524437 A | 9/2011 |
| JP | 2016-528332 A | 9/2016 |

OTHER PUBLICATIONS

International Search Report dated Aug. 20, 2019 in PCT/JP2019/025392 filed on Jun. 26, 2019, 2 pages.
"Gousei Koryo: Kagaku to Shohin Chisiki, zoho shinban (Synthetic fragrance: chemistry and product knowledge, new enlarged edition)", The Chemical Daily Co. Ltd., 2016, pp. 580-582 (4 total pages).

* cited by examiner

*Primary Examiner* — Yate' K Cutliff
(74) *Attorney, Agent, or Firm* — Oblon, McClelland, Maier & Neustadt, L.L.P.

(57) ABSTRACT

A compound, represented by Formula (1): where X represents an isopropyl group or a t-butyl group, and R represents a linear, branched, or cyclic alkyl group having 1 to 5 carbon atoms; provided that one where X is an isopropyl group, and R is a t-butyl group is excluded.

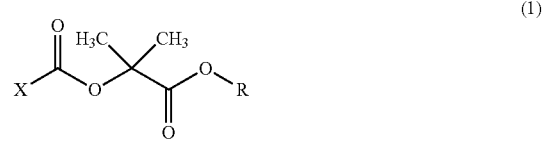

(1)

20 Claims, No Drawings

ISOBUTYRIC ESTER COMPOUND HAVING BUTYRYLOXY GROUP OR PIVALOYLOXY GROUP AT α-POSITION AND FRAGRANCE COMPOSITION

TECHNICAL FIELD

The present invention relates to isobutyric ester compounds having a butyryloxy group or pivaloyloxy group at the α-position and a fragrance composition.

BACKGROUND ART

Some isobutyric esters are known to be compounds useful as fragrances. For example, Non Patent Document 1 describes that various isobutyric esters are mainly used as flavors, and all these isobutyric esters are flavor materials having a fruit scent; specifically, methyl isobutyrate gives a sweet apricot-like scent, propyl isobutyrate gives a strong pineapple-like scent, butyl isobutyrate gives a fresh apple- and banana-like scent, and isoamyl isobutyrate gives a sweet apricot- and pineapple-like scent.

Additionally, Patent Document 1 discloses that, as an isobutyric ester having a bond with oxygen at α-position, a linear or branched alkyl ester having 4 to 12 carbon atoms of α-alkoxyisobutyric acid is useful as a fragrance, and n-hexyl α-ethoxyisobutyrate has a lavender-like aroma.

CITATION LIST

Patent Documents

Patent Document 1: U.S. Pat. No. 3,368,943

Non Patent Document

Non-Patent Document 1: "Gousei Koryo: Kagaku to Shohin Chisiki, zoho shinban (Synthetic fragrance: chemistry and product knowledge, new enlarged edition)", The Chemical Daily Co. Ltd., 2016, pp. 580 to 582

DISCLOSURE OF THE INVENTION

Technical Problem

An object to be solved by the present invention is to provide an isobutyric ester compound having a butyryloxy group or a pivaloyloxy group at the α-position, useful as a fragrance and a fragrance ingredient. Further, another object to be solved by the present invention is to provide a fragrance composition containing the compound as an active ingredient and use of the compound as a fragrance.

Solution to Problem

The present inventors have synthesized various compounds and have made diligent research of the aromas thereof. Thus, the present inventors discovered that particular ester compounds of isobutyric acid having an isobutyryloxy group or a pivaloyloxy group at the α-position are useful as fragrances and fragrance ingredients.

That is, the present invention is as follows.

<1> A compound, represented by Formula (1):

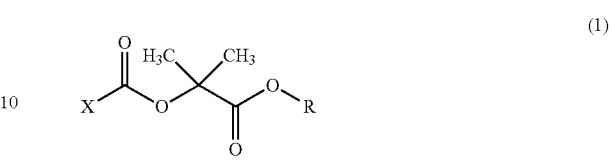

where, in Formula (1), X represents an isopropyl group or a t-butyl group, and R represents a linear, branched, or cyclic alkyl group having 1 to 5 carbon atoms; provided that one where X is an isopropyl group and R is a t-butyl group is excluded.

<2> The compound according to <1>, wherein, in Formula (1), R is selected from the group consisting of a methyl group, an ethyl group, a n-propyl group, an isopropyl group, a n-butyl group, an isobutyl group, a sec-butyl group, a 3-methylbutan-2-yl group, and a cyclopentyl group.

<3> The compound according to <1> or <2>, wherein, in Formula (1), X is an isopropyl group.

<4> The compound according to any one of <1> to <3>, wherein, in Formula (1), X is an isopropyl group, and R is a methyl group.

<5> The compound according to any one of <1> to <3>, wherein, in Formula (1), X is an isopropyl group, and R is an ethyl group.

<6> The compound according to any one of <1> to <3>, wherein, in Formula (1), X is an isopropyl group, and R is a n-propyl group.

<7> The compound according to any one of <1> to <3>, wherein, in Formula (1), X is an isopropyl group, and R is an isopropyl group.

<8> The compound according to any one of <1> to <3>, wherein, in Formula (1), X is an isopropyl group, and R is a n-butyl group.

<9> The compound according to any one of <1> to <3>, wherein, in Formula (1), X is an isopropyl group, and R is an isobutyl group.

<10> The compound according to any one of <1> to <3>, wherein, in Formula (1), X is an isopropyl group, and R is a sec-butyl group.

<11> The compound according to any one of <1> to <3>, wherein, in Formula (1), X is an isopropyl group, and R is a 3-methylbutan-2-yl group.

<12> The compound according to any one of <1> to <3>, wherein, in Formula (1), X is an isopropyl group, and R is a cyclopentyl group.

<13> The compound according to <1> or <2>, wherein, in Formula (1), X is a t-butyl group.

<14> The compound according to any one of <1>, <2>, and <13>, wherein, in Formula (1), X is a t-butyl group, and R is a methyl group.

<15> The compound according to any one of <1>, <2>, and <13>, wherein, in Formula (1), X is a t-butyl group, and R is an ethyl group.

<16> The compound according to any one of <1>, <2>, and <13>, wherein, in Formula (1), X is a t-butyl group, and R is a n-propyl group.

<17> The compound according to any one of <1>, <2>, and <13>, wherein, in Formula (1), X is a t-butyl group, and R is an isopropyl group.

<18> The compound according to any one of <1>, <2>, and <13>, wherein, in Formula (1), X is a t-butyl group, and R is a n-butyl group.

<19> The compound according to any one of <1>, <2>, and <13>, wherein, in Formula (1), X is a t-butyl group, and R is an isobutyl group.

<20> A fragrance composition comprising a compound described in any one of <1> to <19> as an active ingredient.

<21> Use of the compound described in any one of <1> to <19> as a fragrance.

<22> The use according to <21>, wherein the compound described in any one of <4>, <5>, <6>, <7>, <11>, <14>, <15>, and <17> imparts a damascone-like fruity-tone, floral-tone, or woody-tone scent.

Advantageous Effects of Invention

According to the present invention, it is possible to provide an isobutyric ester compound having a butyryloxy group or a pivaloyloxy group at the α-position, useful as a fragrance and a fragrance ingredient. Furthermore, according to the present invention, it is possible to provide a fragrance composition containing the compound as an active ingredient and use of the compound as a fragrance.

DESCRIPTION OF EMBODIMENTS

Compound Represented by Formula (1)

A compound according to an embodiment of the present invention is represented by Formula (1) below. The compound represented by Formula (1) below is also referred to as the "isobutyric ester according to an embodiment of the present invention" or the "compound according to an embodiment of the present invention".

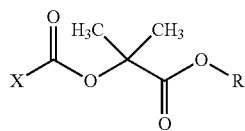

(1)

In Formula (1), X represents an isopropyl group or a t-butyl group (tertiary butyl group), and R represents a linear, branched, or cyclic alkyl group having 1 to 5 carbon atoms; provided that one where X is an isopropyl group, and R is a t-butyl group is excluded.

Specific examples of R include a methyl group, an ethyl group, a n-propyl group, an isopropyl group, a n-butyl group, an isobutyl group (2-methylpropyl group), a sec-butyl group (1-methylpropyl group), a tert-butyl group, a n-pentyl group, a 1-methylbutyl group, a 2-methylbutyl group, a 3-methylbutyl group, a neopentyl group (2,2-dimethylpropyl group), a 2-methylbutan-2-yl group, a 1-ethylpropyl group (3-pentyl group), a 3-methylbutan-2-yl group, a cyclopropyl group, a cyclobutyl group, and a cyclopentyl group.

When R has an asymmetric carbon, the compound according to an embodiment of the present invention may include only one of optical isomers derived therefrom, or may be a mixture including a plurality of optical isomers in any proportion.

The compound represented by Formula (1) is a novel compound.

The isobutyric ester according to an embodiment of the present invention represented by Formula (1), which is useful as a fragrance and a fragrance ingredient, has a mint-like aroma as well as simultaneously exhibits an aroma of a woody tone, floral tone, green tone, or the like due to the difference in the alkyl groups of the ester moiety.

The compound is preferably a compound in which X is an isopropyl group, and R is selected from the group consisting of a methyl group, an ethyl group, a n-propyl group, an isopropyl group, a n-butyl group, an isobutyl group, a sec-butyl group, a 3-methylbutan-2-yl group, and a cyclopentyl group. The compound is also preferably a compound in which X is a t-butyl group, and R is selected from the group consisting of a methyl group, an ethyl group, a n-propyl group, an isopropyl group, a n-butyl group, and an isobutyl group.

Particularly preferably, X is an isopropyl group, and R is a methyl group.

Particularly preferably, X is an isopropyl group, and R is an ethyl group.

Particularly preferably, X is an isopropyl group, and R is a n-propyl group.

Particularly preferably, X is an isopropyl group, and R is an isopropyl group.

Particularly preferably, X is an isopropyl group, and R is a n-butyl group.

Particularly preferably, X is an isopropyl group, and R is an isobutyl group.

Particularly preferably, X is an isopropyl group, and R is a sec-butyl group.

Particularly preferably, X is an isopropyl group, and R is a 3-methylbutan-2-yl group.

Particularly preferably, X is an isopropyl group, and R is a cyclopentyl group.

Particularly preferably, X is a t-butyl group, and R is a methyl group.

Particularly preferably, X is a t-butyl group, and R is an ethyl group.

Particularly preferably, X is a t-butyl group, and R is a n-propyl group.

Particularly preferably, X is a t-butyl group, and R is an isopropyl group.

Particularly preferably, X is a t-butyl group, and R is a n-butyl group.

Particularly preferably, X is a t-butyl group, and R is an isobutyl group.

In an embodiment of the present invention, examples of a compound in which X is an isopropyl group include a compound represented by any of the following formulas (1-1) to (1-18), and particularly preferable compounds include a compound represented by any of the following formulas (1-1) to (1-8), (1-17).

Also, in an embodiment of the present invention, examples of a compound in which X is a t-butyl group include a compound represented by any of the following formulas (2-1) to (2-19), and particularly preferable compounds include a compound represented by any of Formulas (2-1) to (2-6) below.

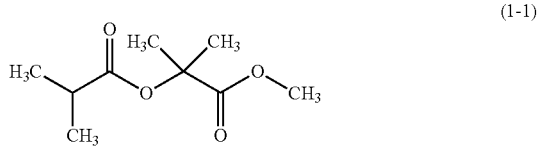

(1-1)

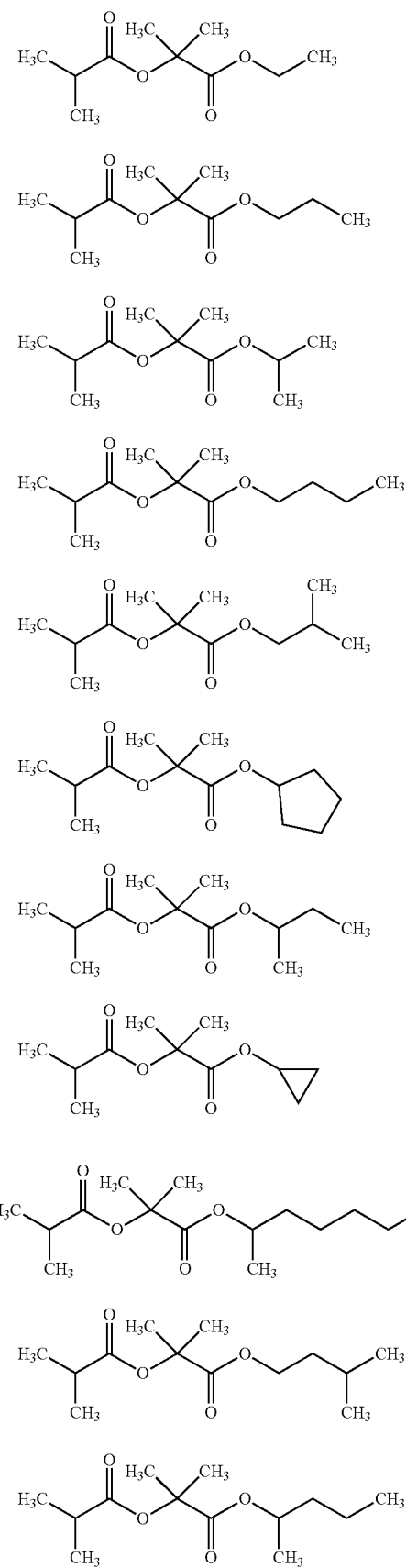
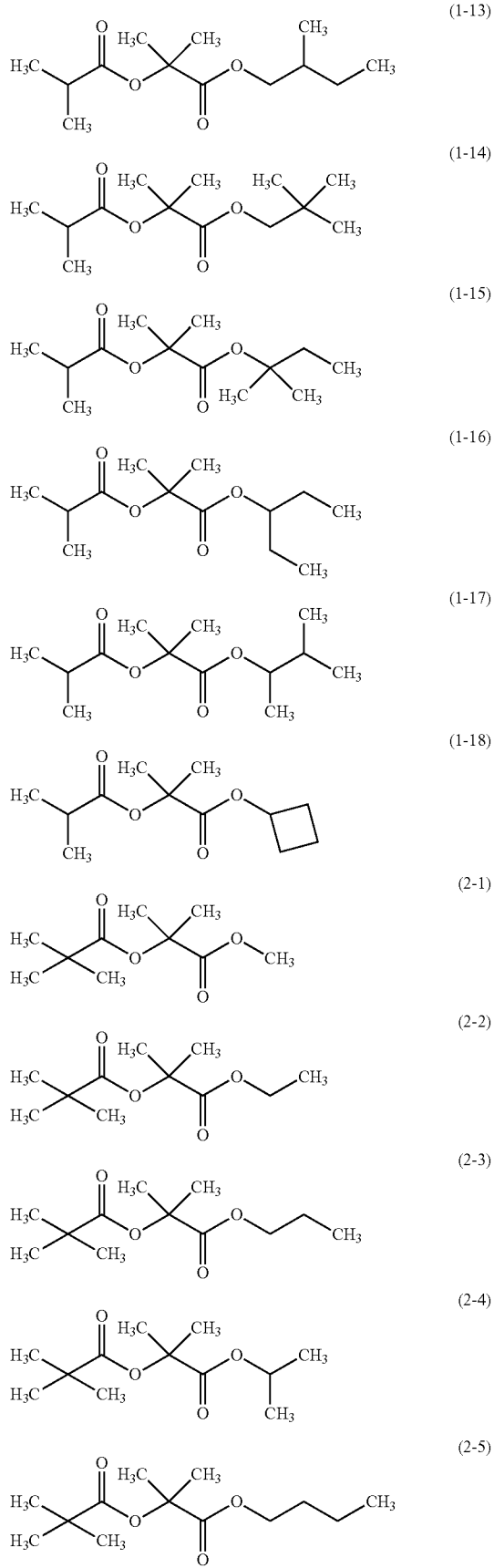

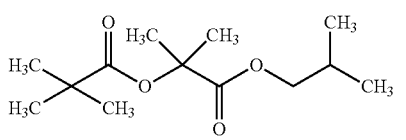
(2-6)

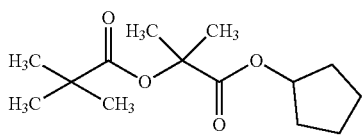
(2-7)

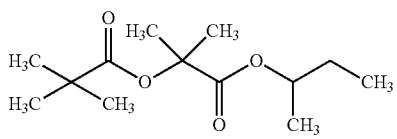
(2-8)

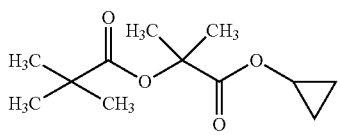
(2-9)

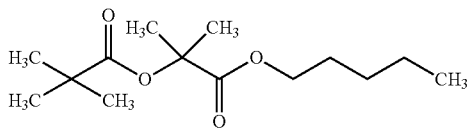
(2-10)

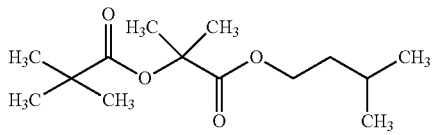
(2-11)

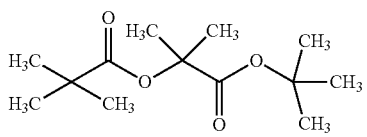
(2-12)

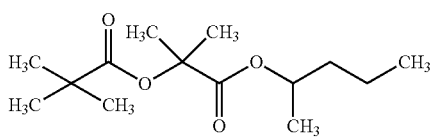
(2-13)

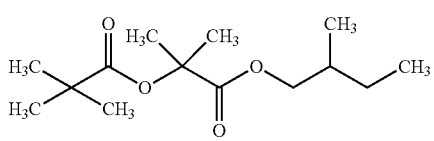
(2-14)

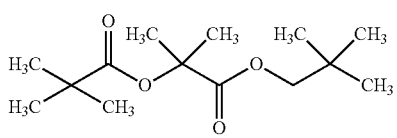
(2-15)

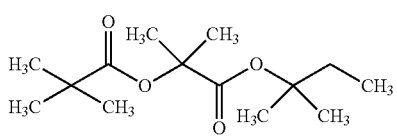
(2-16)

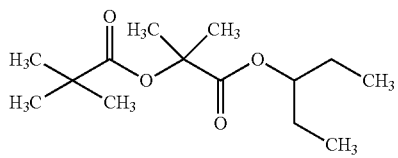
(2-17)

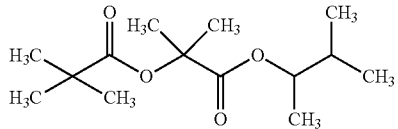
(2-18)

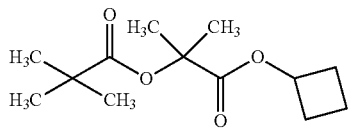
(2-19)

In recent years, there is a trend to focus more on the toxicity and environmental impact of chemicals, and fragrances or fragrance compositions are no exception. There is an increase in the number of cases where a fragrance which has been used in the past is severely restricted in usage conditions or is prohibited from use due to their sensitization properties to a human body, tendency to accumulate in the environment, and the like. Thus, there is a strong demand for a fragrance and a fragrance composition having a lower environmental impact. Accordingly, the fragrance ingredient preferably has excellent biodegradability.

The compound according to an embodiment of the present invention contains a compound excellent in biodegradability, and from the perspective of biodegradability, R is preferably a group selected from the group consisting of a methyl group, an ethyl group, a n-propyl group, an isopropyl group, a n-butyl group, an isobutyl group, a sec-butyl group, a 3-methylbutan-2-yl group, and a cyclopentyl group. Additionally, from the same perspective, R is preferably a group selected from the group consisting of a methyl group, an ethyl group, a n-propyl group, an isopropyl group, a n-butyl group, an isobutyl group, and a cyclopentyl group.

The isobutyric ester according to an embodiment of the present invention is useful as a fragrance because the compound has an excellent aroma as described below. Generally, a fragrance is rarely used alone, and often used in a fragrance compound (fragrance composition) produced by compounding a plurality of fragrances in accordance with the purpose. The isobutyric ester according to an embodiment of the present invention is useful as a fragrance which is to be blended in a fragrance compound (fragrance composition) (also referred to as a "fragrance ingredient"). As the fragrance, one of the compounds represented by Formula (1) above may be used alone or two or more of the compounds may be used in combination.

Additionally, the compound according to an embodiment of the present invention may include a small amount of impurities, by-products, contaminants, and the like as long as the effects of the present invention are not compromised.

The isobutyric ester according to an embodiment of the present invention represented by Formula (1) has a mint-like aroma as well as an aroma of woody-tone, floral-tone, green-tone, or like, and also is excellent in diffusivity. Further, the isobutyric ester according to an embodiment of the present invention represented by any of Formulas (1-1), (1-2), (1-3), (1-4), (1-17), (2-1), (2-2), and (2-4) has a damascone-like fruity-tone, floral-tone, or woody-tone aroma, and also is excellent in diffusivity.

The isobutyric ester according to an embodiment of the present invention may be used alone as a fragrance and added to various perfumery and cosmetics, healthcare and sanitary materials as well as medicinal supplies, household goods, foods, and the like to thereby impart an aroma thereto. Alternatively, the isobutyric ester according to an embodiment of the present invention may be mixed with another fragrance ingredient or the like to prepare a fragrance composition (fragrance compound) described below, which may be blended into a variety of products to impart an aroma. Among these, from the perspective of obtaining an intended aroma, it is preferred that the compound according to an embodiment of the present invention be blended in a fragrance composition as a fragrance ingredient and the fragrance composition be blended in a product to perfume the product.

Fragrance Composition

The fragrance composition (fragrance compound) according to an embodiment of the present invention contains the isobutyric ester according to an embodiment of the present invention as an active ingredient. Note that the isobutyric ester according to an embodiment of the present invention is not particularly limited as long as it contains at least one isobutyric ester according to an embodiment of the present invention, and two or more isobutyric esters may be contained.

The fragrance composition according to an embodiment of the present invention is only required to contain the isobutyric ester according to an embodiment of the present invention as an active ingredient, and other ingredients are not particularly limited. However, the fragrance composition preferably contains another fragrance ingredient (hereinafter, also referred to as a "known fragrance").

Note that the "fragrance composition (fragrance compound)" is a composition that is added to various perfumery and cosmetics, medicinal supplies, foods, beverages, and the like to impart an aroma thereto, or a composition that is used as it is in a perfume or the like. The fragrance composition may contain an additive such as a solvent, as required, in addition to the known fragrance.

The amount of the isobutyric ester according to an embodiment of the present invention blended depends on the type of the isobutyric ester according to an embodiment of the present invention, the type of aroma intended, the intensity of the aroma, and the like. The amount of the isobutyric ester according to an embodiment of the present invention represented by Formula (1) in the fragrance composition is preferably 0.001 mass % or greater, more preferably 0.01 mass % or greater, even more preferably 0.1 mass % or greater, preferably 90 mass % or less, more preferably 70 mass % or less, and even more preferably 50 mass % or less.

The known fragrance is not particularly limited as long as it is a known fragrance component, and a wide range of fragrances can be used. For example, one or two or more of the following fragrances can be selected and used at any mixing ratio.

Examples thereof include hydrocarbons such as limonene, α-pinene, β-pinene, terpinene, cedrene, longifolene, and valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-t-butylcyclohexanol, 4-methyl-2-(2-methylpropyl)tetrahydro-2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol; phenols such as eugenol, thymol, and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobronyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and FRUTTATE; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, and cyclohexedecanone; acetals and ketals such as acetoaldehyde ethylphenylpropyl acetal, citraldiethyl acetal, phenylacetoaldehyde glycerin acetal, and ethylacetoacetate ethyleneglycol ketals; ethers such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2,1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, sandalwood, vetiver, patchouli, and labdanum; and other fragrance materials such as synthetic fragrances.

In addition, the fragrance composition may also contain, as components besides the fragrance ingredients, a surfactant such as polyoxyethylene lauryl sulfate ether; a solvent such as dipropylene glycol, diethyl phthalate, ethylene glycol, propylene glycol, methyl myristate, triethyl citrate, or the like; an antioxidant; a coloring agent, and the like.

The isobutyric ester according to an embodiment of the present invention represented by formula (1), which has a mint-like aroma and simultaneously has an aroma of a woody note, a floral note, a green note, or the like, can impart a natural woody note, a floral note, or a green note in addition to the mint note when combined with a known fragrance. Thus, the isobutyric ester is usefully added to various perfumery and cosmetics, healthcare and sanitary materials as well as to medicinal supplies, household goods, foods, and the like to thereby impart an aroma thereto. The isobutyric ester according to an embodiment of the present invention represented by any of formulas (1-1), (1-2), (1-3), (1-4), (1-17), (2-1), (2-2), and (2-4), are usefully combined with a known fragrance or the like to thereby impart an aroma because of having a damascone-like fruity-tone, floral-tone, or woody-tone aroma.

Examples of products to which a fragrance composition containing the isobutyric esters according to an embodiment of the present invention represented by Formula (1) can be added to impart an aroma and improve the aroma of the blend object include various products such as perfumery and cosmetics, health and sanitary materials, miscellaneous goods, beverages, foods, quasi-pharmaceutical products, and medicinal supplies; the fragrance composition can be used as an aroma component in, for example, fragrance products such as perfumes and colognes; hair cosmetics such as shampoos, rinses, hair tonics, hair creams, mousses, gels, pomades, sprays, and the like; skin cosmetics such as skin lotions, essences, creams, milky lotions, packs, foundations, face powders, lipsticks, and various make-up products; various health and sanitary detergents such as dish washing detergents, laundry detergents, softeners, disinfecting detergents, anti-odor detergents, indoor fragrances, furniture cares, glass cleaners, furniture cleaners, floor cleaners, disinfectants, insecticides, bleaching agents, bactericides, repellants, and the like; quasi-pharmaceutical products such as toothpastes, mouthwashes, bath additives, antiperspirant products, and perming liquids; miscellaneous goods such as toilet paper and tissue paper; medicinal supplies; foods, and the like.

The amount of the fragrance composition blended in the product is not particularly limited, and the amount of the fragrance composition blended can be selected over a wide range, depending on the type, nature, and sensory benefits of the product to be perfumed. For example, the amount may be 0.00001 mass % or greater, preferably 0.0001 mass % or greater, more preferably 0.001 mass % or greater. In the case of a fragrance such as perfume or the like, for example, the amount may be 100 mass %, preferably 80 mass % or less, more preferably 60 mass % or less, and even more preferably 40 mass % or less.

Method for Producing Isobutyric Ester of Present Invention

The production method of the isobutyric ester according to an embodiment of the present invention represented by Formula (1) is not particularly limited and may be appropriately selected from known methods and used.

Examples thereof include a method including reacting an α-hydroxyisobutyric ester with an acylating agent in the presence or absence of a catalyst to acylate the hydroxyl group at the α-position. Examples of the acylating agent to be used include carboxylic acids such as isobutyric acid and pivalic acid, carboxylic anhydrides such as isobutyric anhydride and pivalic anhydride, carboxylic halides such as isobutyryl chloride, isobutyryl bromide, pivaloyl chloride, and pivaloyl bromide, and ketene compounds such as dimethyl ketene. In addition, two or more acylating agents selected from these may be used in combination at any ratio.

The reaction formula when a carboxylic acid, a carboxylic acid anhydride, or a carboxylic acid halide is used is shown as Formula (2) below.

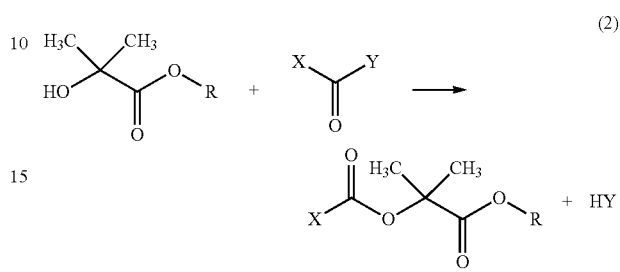

In Formula (2), X represents an isopropyl group or a t-butyl group, and R represents a linear, branched, or cyclic alkyl group having 1 to 5 carbon atoms. Y depends on the type of the acylating agent and represents, for example, a hydroxyl group, an isobutyryloxy group, a pivaloyloxy group, chlorine, bromine, iodine, or the like.

The reaction formula when a ketene is used is shown as Formula (3) below.

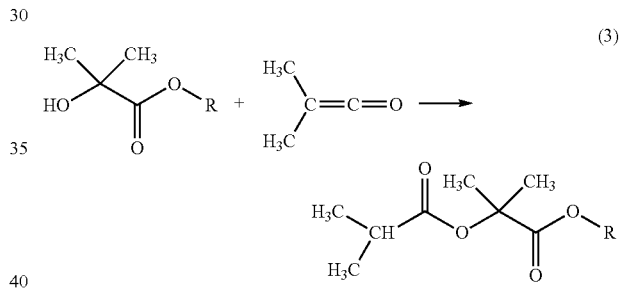

In Formula (3), R represents a linear, branched, or cyclic alkyl group having 1 to 5 carbon atoms.

Further, a target α-butyryloxyisobutyric ester or α-pivaloyloxyisobutyric ester can be produced by transesterifying α-butyryloxyisobutyric ester or α-pivaloyloxyisobutyric ester with an alcohol of different kinds in the presence of a catalyst. The reaction formula for this reaction is shown as Formula (4) below.

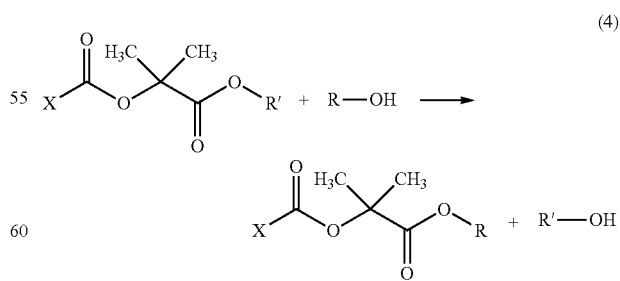

In Formula (4), X represents an isopropyl group or a t-butyl group, and R represents a linear, branched, or cyclic alkyl group having 1 to 5 carbon atoms. R' is not particularly limited as long as it is an alkyl group different from R.

Similarly, a target α-butyryloxyisobutyric ester or α-pivaloyloxyisobutyric ester can be produced by esterifying α-butyryloxyisobutyric acid or α-pivaloyloxyisobutyric acid with an alcohol in the presence of a catalyst. The reaction formula for this reaction is shown as Formula (5) below.

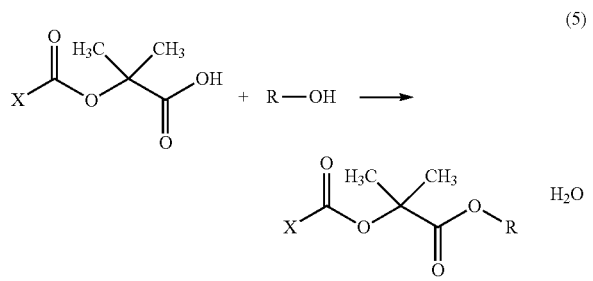

(5)

In Formula (5), X represents an isopropyl group or a t-butyl group, and R represents a linear, branched, or cyclic alkyl group having 1 to 5 carbon atoms.

Known catalysts, reaction methods, reaction conditions, and reaction apparatuses can be used as the catalyst, reaction method, reaction conditions, reaction apparatuses, and the like to be used for these reactions, and there are no particular limitation thereon. In addition, as a method for purifying the obtained compound of Formula (1), a known purification method can be used, and there is no limitation thereon.

EXAMPLES

Hereinafter, the present invention will be described in further detail with reference to examples, but the present invention is not limited to these examples.

The reaction performance was evaluated according to the following expression. Reaction yield (%)=[(number of moles of product ester in reaction solution)/(number of moles of raw material ester in solution fed)]×100%

Gas Chromatography (GC) Analysis Conditions

Apparatus: GC-2010 (available from Shimadzu Corporation, trade name)
Detector: FID
Column: DB-1 (capillary column available from J&W Scientific, Inc., trade name) (0.25 mmφ×60 m×0.25 μm)

NMR Spectrum Analysis

Identification of the ester was performed by $^1$H-NMR measurement and $^{13}$C-NMR measurement. The measurement conditions are shown below.
Apparatus: ECA500 (available from JEOL Ltd., trade name)
[$^1$H-NMR]
  Nuclide: $^1$H
  Measurement frequency: 500 MHz
  Measurement sample: 5% CDCl$_3$ solution
[$^{13}$C-NMR]
  Nuclide: $^{13}$C
  Measurement frequency: 125 MHz
  Measurement sample: 5% CDCl$_3$ solution Gas Chromatograph-Mass Spectrometry (GC-MS Analysis)

Identification of the compounds was also performed by determining the molecular weight by GC-MS measurement (chemical ionization method [CI+], high resolution mass spectrometry [millimass]). The measurement conditions are shown below.

GC apparatus: Agilent 7890A (available from Agilent Technologies, trade name) GC measurement conditions
Column: DB-1 (capillary column available from J&W Scientific, Inc., trade name) (0.25 mmφ×30 m×0.25 μm)
MS apparatus: JMS-T100GCV (available from JEOL Ltd., trade name)
MS measurement conditions: chemical ionization method
Detector conditions: 200 eV, 300 μA
Reagent gas: isobutane The exact mass values of fragments detected in the protonated state by the chemical ionization method and the chemical composition formula thus attributed were described.

Product Isolation by Chromatograph Method

Materials described below were used for product isolation by a chromatograph method.
Filler: Wakogel C-200 (available from Wako Pure Chemical Industries, Ltd., trade name)
Development solvent: ethyl acetate-hexane Example 1: Synthesis of Methyl α-Isobutyryloxyisobutyrate 20.0 g of methyl α-hydroxyisobutyrate (available from Mitsubishi Gas Chemical Company, Inc.), 32.1 g of isobutyric anhydride (available from Wako Pure Chemical Industries, Ltd.), 13.4 g of pyridine (available from Wako Pure Chemical Industries, Ltd.), 2.1 g of 4-dimethylaminopyridine (available from Wako Pure Chemical Industries, Ltd.), and 31 g of dichloromethane (available from Wako Pure Chemical Industries, Ltd.) were loaded in a 200 ml glass round bottom flask equipped with a condenser and a stirrer, and reacted under stirring at room temperature to 40° C. for 6 hours. From the GC analysis of the reaction solution, it was confirmed that methyl α-hydroxyisobutyrate was completely consumed by the reaction with isobutyric anhydride and that methyl α-isobutyryloxyisobutyrate was obtained at a reaction yield of 92% by the reaction of Formula (6) below. Then, a washing operation was performed three times with a 10% aqueous solution of sodium hydrogen carbonate, twice with a saturated aqueous solution of ammonium chloride, and twice with a saturated aqueous solution of sodium chloride. The washed product was dried over magnesium sulfate and then concentrated. Subsequently, distillation was performed under reduced pressure to obtain 15.3 g of methyl α-isobutyryloxyisobutyrate (purity by GC analysis (hereinafter, also referred to as GC purity): 99.9%) as the fraction at 81 hPa and 80° C. The results of the NMR spectral analysis and GC-MS analysis of the product are shown below.

[Methyl α-isobutyryloxyisobutyrate]

$^1$H NMR (500 MHz, CDCl$_3$) δ 1.16 (6H, d, J=7.0 Hz), 1.54 (6H, s), 2.54 (1H, sept, J=7.0 Hz), 3.72 (3H, s)

$^{13}$C NMR (125 MHz, CDCl$_3$) δ 18.7, 24.6, 33.9, 52.3, 77.7, 173.2, 176.1

Exact mass: 189.12751 (C$_9$H$_{16}$O$_4$, parent peak), 157.08686 (C$_8$H$_{12}$O$_3$)

(6)

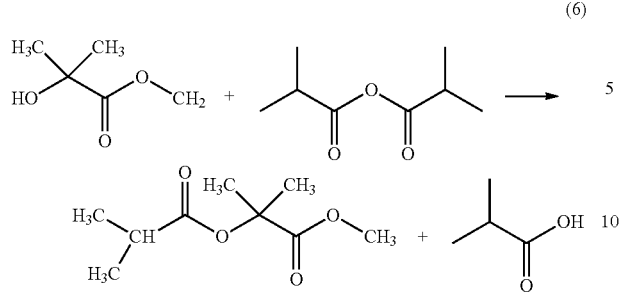

Example 2: Synthesis of Methyl α-Pivaloyloxyisobutyrate

Using a reaction apparatus similar to that of Example 1, a reaction was performed using 19.9 g of methyl α-hydroxyisobutyrate (available from Mitsubishi Gas Chemical Company, Inc.), 37.8 g of pivalic anhydride (available from Wako Pure Chemical Industries, Ltd.), 13.3 g of pyridine (available from Wako Pure Chemical Industries, Ltd.), and 2.1 g of 4-dimethylaminopyridine (available from Wako Pure Chemical Industries, Ltd.) at room temperature to 70° C. for 129 hours. From the GC analysis of the reaction solution, it was confirmed that methyl α-hydroxyisobutyrate was substantially consumed by the reaction with pivalic anhydride and that methyl α-pivaloyloxyisobutyrate was obtained by the reaction of Formula (7) below. Then, the operation was performed in the same manner as in Example 1, and finally, methyl α-pivaloyloxyisobutyrate was obtained with column chromatography (GC purity: 99.6%). The results of the NMR spectral analysis and GC-MS analysis of the product are shown below.

[Methyl α-pivaloyloxyisobutyrate]
$^1$H NMR (500 MHz, CDCl$_3$) δ 1.20 (9H, s), 1.54 (6H, s), 3.71 (3H, s)
$^{13}$C NMR (125 MHz, CDCl$_3$) δ 24.4, 26.9, 38.5, 52.2, 77.6, 173.2, 177.4
Exact mass: 203.13468 (C$_{10}$H$_{18}$O$_4$, parent peak), 171.10112 (C$_9$H$_{14}$O$_3$)

(7)

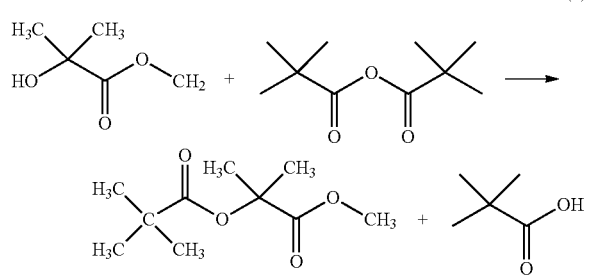

Reference Example 1: Synthesis of Ethyl α-hydroxyisobutyrate

In a 300 ml glass flask equipped with a distillation tube, 56.7 g of methyl α-hydroxyisobutyrate (available from Mitsubishi Gas Chemical Company, Inc.), 33.2 g of ethanol (available from Wako Pure Chemical Industries, Ltd.), and 0.92 g of titanium tetraethoxide (available from Wako Pure Chemical Industries, Ltd.) were loaded. A transesterification reaction was performed under normal pressure with heating and refluxing. The reaction was performed for 96 hours while methanol produced was extracted out of the system. As a result, ethyl α-hydroxyisobutyrate was obtained at a reaction yield of 97%. After water was added to the reaction system to inactivate the catalyst, distillation was performed under reduced pressure to obtain 46.9 g of ethyl α-hydroxyisobutyrate (GC purity: 99.6%) as the fraction at 71 mmHg and 77° C.

Reference Examples 2 to 8: Synthesis of Various α-Hydroxyisobutyric Esters

Using the same reaction apparatus as in Reference Example 1, an appropriate amount of methyl α-hydroxyisobutyrate (available from Mitsubishi Gas Chemical Company, Inc.) was transesterified with a different alcohol (n-propanol, isopropanol, n-butanol, isobutanol, sec-butanol, 3-methyl-2-butanol, cyclopentanol) in the presence of a suitable catalyst such as a titanium tetraalkoxide and/or sodium alkoxide, and in some cases in the co-presence of a solvent such as hexane or toluene, under appropriate reaction conditions with heating. The transesterification reaction was completed while methanol produced by the reaction was extracted out of the system by distillation or through azeotrope with a reaction solvent under the reaction conditions. The same separation operation as in Reference Example 1 was performed to obtain each of the following α-hydroxyisobutyric ester. The GC purity of the obtained isobutyric ester is also shown.

n-propyl α-hydroxyisobutyrate (GC purity: 99.8%)
Isopropyl α-hydroxyisobutyrate (GC purity: 99.6%)
n-butyl α-hydroxyisobutyrate (GC purity: 99.9%)
Isobutyl α-hydroxyisobutyrate (GC purity: 99.6%)
sec-butyl α-hydroxyisobutyrate (GC purity: 99.6%)
3-methylbutan-2-yl α-hydroxyisobutyrate (GC purity: 99.7%)
Cyclopentyl α-hydroxyisobutyrate (GC purity: 99.8%)

Example 3: Synthesis of Ethyl α-Isobutyryloxyisobutyrate>

Using a reaction apparatus similar to that of Example 1, a reaction was performed using ethyl α-hydroxyisobutyrate prepared in Reference Example 1, isobutyric anhydride (available from Wako Pure Chemical Industries, Ltd.), pyridine (available from Wako Pure Chemical Industries, Ltd.), and 4-dimethylaminopyridine (available from Wako Pure Chemical Industries, Ltd.) in appropriate amounts. The operation was performed in the same manner as in Example 1 to obtain ethyl α-isobutyryloxyisobutyrate (GC purity: 99.6%) as the fraction at 20 hPa and 90° C. by distillation under reduced pressure. The results of the NMR spectral analysis and GC-MS analysis of the product are shown below.

[Ethyl α-isobutyryloxyisobutyrate]
$^1$H NMR (500 MHz, CDCl$_3$) δ 1.16 (6H, d, J=7.0 Hz), 1.25 (3H, t, J=7.0 Hz), 1.54 (6H, s), 2.54 (1H, sept, J=7.0 Hz), 4.17 (2H, q, J=7.0 Hz)
$^{13}$C NMR (125 MHz, CDCl$_3$) δ 14.0, 18.7, 24.5, 33.8, 61.1, 77.7, 172.6, 175.9
Exact mass: 203.13228 (C$_{10}$H$_{18}$O$_4$, parent peak), 157.08761 (C$_8$H$_{12}$O$_3$)

Examples 4 to 10: Synthesis of α-Isobutyryloxyisobutyric Ester

Using a reaction apparatus similar to that of Example 3, a reaction was performed using each α-hydroxyisobutyric ester prepared in Reference Examples 2 to 8, isobutyric anhydride (available from Wako Pure Chemical Industries, Ltd.), pyridine (available from Wako Pure Chemical Industries, Ltd.), and 4-dimethylaminopyridine (available from Wako Pure Chemical Industries, Ltd.) in appropriate amounts. The operation was performed in the same manner as in Example 1 to obtain each of α-isobutyryloxyisobutyric esters described below by distillation under reduced pressure. The GC purity of the resulting esters, the distillation conditions during the distillation under reduced pressure, and the results of NMR spectral analysis and GC-MS analysis are also shown.

[n-propyl α-isobutyryloxyisobutyrate]
GC purity: 98.0%, distillation condition: 20 hPa, 105 to 106° C.
$^1$H NMR (500 MHz, CDCl$_3$) δ 0.94 (3H, t, J=7.0 Hz), 1.16 (6H, d, J=7.0 Hz), 1.55 (6H, s), 1.65 (2H, m), 2.54 (1H, sept, J=7.0 Hz), 4.07 (2H, t, J=6.5 Hz)
$^{13}$C NMR (125 MHz, CDCl$_3$) δ 10.3, 18.7, 21.8, 24.6, 33.9, 66.7, 77.8, 172.7, 175.9
Exact mass: 217.14767 ($C_{11}H_{20}O_4$, parent peak), 157.08780 ($C_8H_{12}O_3$)

[Isopropyl α-isobutyryloxyisobutyrate]
GC purity: 99.7%, distillation condition: 18 hPa, 91 to 92° C.
$^1$H NMR (500 MHz, CDCl$_3$) δ 1.16 (6H, d, J=7.0 Hz), 1.22 (6H, d, J=6.0 Hz), 1.53 (6H, s), 2.53 (1H, sept, J=7.0 Hz), 5.03 (1H, sept, J=7.0 Hz)
$^{13}$C NMR (125 MHz, CDCl$_3$) δ 18.8, 21.6, 24.5, 33.9, 68.5, 77.8, 172.1, 175.8
Exact mass: 217.14808 ($C_{11}H_{20}O_4$, parent peak), 157.08808 ($C_8H_{12}O_3$)

[n-butyl α-isobutyryloxyisobutyrate]
GC purity: 99.7%, distillation condition: 18 hPa, 113° C.
$^1$H NMR (500 MHz, CDCl$_3$) δ 0.93 (3H, t, J=7.0 Hz), 1.16 (6H, d, J=7.0 Hz), 1.37 (2H, q, J=7.0 Hz), 1.54 (6H, s), 1.60 (2H, m), 2.54 (1H, sept, J=7.0 Hz), 4.11 (2H, t, J=6.5 Hz)
$^{13}$C NMR (125 MHz, CDCl$_3$) δ 13.6, 18.7, 19.0, 24.6, 30.5, 33.9, 65.0, 77.8, 172.7, 175.9
Exact mass: 231.16311 ($C_{12}H_{22}O_4$, parent peak), 157.08832 ($C_8H_{12}O_3$)

[Isobutyl α-isobutyryloxyisobutyrate]
GC purity: 99.1%, distillation condition: 21 hPa, 111 to 112° C.
$^1$H NMR (500 MHz, CDCl$_3$) δ 0.93 (6H, d, J=6.5 Hz), 1.17 (6H, d, J=7.0 Hz), 1.55 (6H, s), 1.93 (1H, m, J=6.5 Hz), 2.54 (1H, sept, J=7.0 Hz), 3.90 (2H, d, J=7.0 Hz)
$^{13}$C NMR (125 MHz, CDCl$_3$) δ 18.7, 19.0, 24.6, 27.6, 33.9, 71.2, 77.8, 172.7, 175.9
Exact mass: 231.16636 ($C_{12}H_{22}O_4$, parent peak), 157.08929 ($C_8H_{12}O_3$)

[Secondary butyl α-isobutyryloxyisobutyrate]
GC purity: 99.9%
$^1$H NMR (500 MHz, CDCl$_3$) δ 0.89 (3H, t, J=7.5 Hz), 1.16 (6H, d, J=7.0 Hz), 1.18 (3H, d, J=6.0 Hz), 1.51-1.63 (2H, m), 1.53 (3H, s), 1.54 (3H, s), 2.53 (1H, sep, J=7.0 Hz), 4.86 (1H, sext, J=6.0 Hz)
$^{13}$C NMR (125 MHz, CDCl$_3$) δ 9.5, 18.7, 18.8, 19.1, 24.4, 24.6, 28.6, 33.8, 73.0, 77.8, 172.2, 175.8
Exact mass: 231.16157 ($C_{12}H_{22}O_4$, parent peak), 175.10069 ($C_8H_{14}O_4$)

[3-Methylbutan-2-yl α-hydroxyisobutyrate]
GC purity: 98.7%
$^1$H NMR (500 MHz, CDCl$_3$) δ 0.906 (6H, d, J=6.5 Hz), 1.144 (3H, d, J=6.0 Hz), 1.161 (3H, d, J=7.5 Hz), 1.167 (3H, d, J=7.0 Hz), 1.550 (3H, s), 1.532 (3H, s), 1.785 (1H, sept-d, J=6.75 Hz, 5.5 Hz), 2.534 (1H, sept, J=7.0 Hz), 4.762 (1H, qd, J=6.0 Hz, 6.0 Hz)
$^{13}$C NMR (125 MHz, CDCl$_3$) δ 16.43, 17.97, 18.18, 18.87, 19.00, 24.48, 24.97, 32.71, 34.03, 76.17, 78.08, 172.34, 175.89
Exact mass: 245.17754 ($C_{13}H_{24}O_4$, parent peak), 175.10033 ($C_8H_{14}O_4$)

[Cyclopentyl α-isobutyryloxyisobutyrate]
GC purity: 99.5%, distillation condition: 12 hPa, 121° C.
$^1$H NMR (500 MHz, CDCl$_3$) δ 1.16 (6H, d, J=7.0 Hz), 1.52 (6H, s), 1.58 (2H, m), 1.69 (2H, m), 1.71 (2H, m), 1.82 (2H, m), 2.53 (1H, sept, J=7.0 Hz), 5.19 (1H, m)
$^{13}$C NMR (125 MHz, CDCl$_3$) δ 18.7, 23.6, 24.4, 32.3, 33.8, 77.8, 77.9, 172.3, 175.7
Exact mass: 243.16211 ($C_{13}H_{22}O_4$, parent peak), 175.10145 ($C_8H_{14}O_4$)

Examples 11 to 15: Synthesis of α-Pivaloyloxyisobutyric Ester

Using a reaction apparatus similar to that of Examples 4 to 10, a reaction was performed using each α-hydroxyisobutyric ester prepared in Reference Examples 1 to 5, pivalic anhydride (available from Wako Pure Chemical Industries, Ltd.), pyridine (available from Wako Pure Chemical Industries, Ltd.), and 4-dimethylaminopyridine (available from Wako Pure Chemical Industries, Ltd.) in appropriate amounts. The operation was performed in the same manner as in Example 1 to finally obtain each of the following α-pivaloyloxyisobutyric esters with column chromatograph. The GC purity of the resulting esters and the results of NMR spectral analysis and GC-MS analysis are shown below.

[Ethyl α-pivaloyloxyisobutyrate]
GC purity: 99.9%
$^1$H NMR (500 MHz, CDCl$_3$) δ 1.20 (9H, s), 1.24 (3H, t, J=7.0 Hz), 1.53 (6H, s), 4.16 (q, 2H, J=7.0 Hz)
$^{13}$C NMR (125 MHz, CDCl$_3$) δ 14.0, 24.5, 26.9, 38.5, 61.1, 77.7, 172.7, 177.3
Exact mass: 217.14615 ($C_{11}H_{20}O_4$, parent peak), 171.10231 ($C_9H_{14}O_3$)

[n-propyl α-pivaloyloxyisobutyrate]
GC purity: 99.2%
$^1$H NMR (500 MHz, CDCl$_3$) δ 0.94 (3H, t, J=7.0 Hz), 1.20 (9H, s), 1.54 (6H, s), 1.62-1.66 (2H, m), 4.07 (2H, t, J=6.5 Hz)
$^{13}$C NMR (125 MHz, CDCl$_3$) δ 10.3, 21.9, 24.5, 26.9, 38.6, 66.7, 77.7, 172.8, 177.3
Exact mass 231.16132 ($C_{12}H_{22}O_4$, parent peak), 171.10264 ($C_9H_{14}O_3$)

[Isopropyl α-pivaloyloxyisobutyrate]
GC purity: 99.9%
$^1$NMR (500 MHz, CDCl$_3$) δ 1.20 (9H, s), 1.21 (6H, d, J=6.0 Hz), 1.52 (6H, s), 5.02 (1H, sept, J=6.0 Hz)
$^{13}$C NMR (125 MHz, CDCl$_3$) δ 21.6, 24.4, 26.9, 38.5, 68.4, 77.7, 172.1, 177.1
Exact mass: 231.16334 ($C_{12}H_{22}O_4$, parent peak), 171.10296 ($C_9H_{14}O_3$)

[n-butyl α-pivaloyloxyisobutyrate]
GC purity: 99.8%
$^1$H NMR (500 MHz, CDCl$_3$) δ 0.93 (3H, t, J=7.5 Hz), 1.20 (9H, s), 1.37 (2H, q, J=7.0 Hz), 1.53 (6H, s), 1.60 (2H, quint, J=7.0 Hz), 4.11 (2H, t, J=7.0 Hz)
$^{13}$C NMR (125 MHz, CDCl$_3$) δ 13.6, 19.0, 24.5, 26.9, 30.4, 38.5, 64.9, 77.7, 172.8, 177.2

Exact mass: 245.17783 ($C_{13}H_{24}O_4$, parent peak), 171.10388 ($C_9H_{14}O_3$)

[Isobutyl α-pivaloyloxyisobutyrate]

GC purity: 99.2%

$^1$H NMR (500 MHz, CDCl$_3$) δ 0.93 (6H, d, J=6.5 Hz), 1.20 (9H, s), 1.54 (6H, s), 1.93 (1H, m, J=6.5 Hz), 3.89 (2H, d, J=6.5 Hz)

$^{13}$C NMR (125 MHz, CDCl$_3$) δ 19.0, 24.5, 26.9, 27.6, 38.5, 71.1, 77.7, 172.7, 177.2

Exact mass: 245.17768 ($C_{13}H_{24}O_4$, parent peak), 171.10419 ($C_9H_{14}O_3$)

The results of aroma evaluation performed by perfumers for the various α-isobutyryloxyisobutyric esters obtained by the method described above are shown in Table 1.

TABLE 1

| | Isobutyric ester according to an embodiment of the present invention | Aroma evaluation |
|---|---|---|
| Example 1 | (structure) | Mint-like aroma<br>Grapefruit-like bitter aroma<br>Patchouli-like smoky and woody aroma<br>Vetiver-like woody aroma<br>Damascone-like woody aroma |
| Example 3 | (structure) | Fresh mint-like aroma<br>Smoky, bitter and woody aroma<br>Green aroma<br>Fruity and rose-like floral aroma<br>(damascone-like) |
| Example 4 | (structure) | Fresh mint-like aroma<br>Green rose like floral aroma<br>White floral aroma<br>Damascone-like fruity aroma |
| Example 5 | (structure) | Fresh mint-like aroma<br>Spicy and fruity rose-like aroma<br>(damascone-like)<br>White floral aroma |
| Example 6 | (structure) | Fresh mint-like aroma<br>Muscat-like fruity aroma<br>Metallic aroma<br>Floral green aroma |
| Example 7 | (structure) | Fresh mint-like aroma<br>Sweet fruity aroma Green aroma<br>White floral aroma |
| Example 8 | (structure) | Rose-like and hyacinth-like green aroma<br>Balsamic aroma<br>Aldehydic aroma |
| Example 9 | (structure) | Muguet-like floral aroma<br>Rose-like floral aroma<br>(damascone-like)<br>Marine aroma<br>Coconut-like sweet and fruity aroma<br>Mint-like green aroma |
| Example 10 | (structure) | Fresh mint-like aroma<br>Sweet honey-like aroma<br>Myrrha-like rosy floral aroma<br>Green aroma |

The results of aroma evaluation performed by perfumers for the various α-pivaloyloxyisobutyric esters obtained by the method described above are shown in Table 2.

Menthol, menthone, and carvone, having a mint note and (E)-α-damascone and (E)-β-damascenone, having a fruity note, were selected as representative examples of existing

TABLE 2

| | Isobutyric ester according to an embodiment of the present invention | Aroma evaluation |
|---|---|---|
| Example 2 | (structure) | Fresh mint-like aroma<br>Spicy aroma<br>Floral, sweet and woody aroma<br>(damascone-like) |
| Example 11 | (structure) | Fresh mint-like aroma<br>Fruity, woody, and rose-like floral aroma<br>(damascone-like) |
| Example 12 | (structure) | Fresh mint-like aroma<br>Citrus aroma<br>Citronella-like herbal aroma |
| Example 13 | (structure) | Fresh mint-like aroma<br>Fruity floral aroma<br>(damascone-like)<br>White floral aroma |
| Example 14 | (structure) | Mint-like aroma<br>Green apple-like fruity aroma<br>Spicy aroma |
| Example 15 | (structure) | Mint-like aroma<br>Coconut-like fruity aroma<br>Citronella-like herbal aroma |

Biodegradability Evaluation of Fragrance Material

One of methods for evaluating biodegradability of a compound is the OECD test guideline 301 C. In accordance with the method, assessment of biodegradability is possible for the compound from the biochemical oxygen demand and the actual rate of oxygen uptake in an aqueous solution in which the compound and aerobic microorganisms coexist.

Calculation software "Biowin5" and "Biowin6" is known and used in a method for easily and accurately estimating the probability of biodegradation of the compound in compliance with this test method.

The software is available to the public as one of modules of calculation software called "The Estimations Programs Interface for Windows version 4.1", created by the United States Environmental Protection Agency (EPA) for the purpose of evaluating the environmental effects of chemical substances, and is used in the compound classification for The Globally Harmonized System of Classification and Labelling of Chemicals (GHS) and the review of new chemical substances by the United States Environmental Protection Agency. This software was used to evaluate the difference in biodegradability between existing fragrance materials and the compounds according to an embodiment of the present invention.

fragrance materials similar to the compounds according to an embodiment of the present invention, and evaluated along with the compounds according to an embodiment of the present invention. The SMILES formulas used for input to the software and the output results of the probabilities of good degradability by "Biowin5 (linear prediction model)" and "Biowin6 (non-linear prediction model)" are shown in Tables 3 to 4. A larger value of the results indicates better degradability: for a value of 0.5 or more, the compound was rated as having good degradability (symbol "A" in the table), and for a value of less than 0.5, the compound was rated as having low degradability (symbol "B" in the table).

From Table 3 to Table 4, the results obtained show that the compounds according to an embodiment of the present invention were expected to have good biodegradability with respect to menthol, menthone, carvone, (E)-α-damascone, and (E)-β-damascenone, which were the existing fragrance materials similar to the compounds according to an embodiment of the present invention. The results indicated that the compounds according to an embodiment of the present invention are easily biodegraded after being released into the environment as fragrances, and thus exhibited a lower impact on the environment.

TABLE 3

| | Structural formula | SMILES | Biowin5 Degradation probability | Score | Biowin6 Degradation probability | Score |
|---|---|---|---|---|---|---|
| Example 1 | | COC(C(C)(C)OC(C(C)C)=O)=O | 0.859 | A | 0.915 | A |
| Example 3 | | CC(C(OCC)=O)(C)OC(C(C)C)=O | 0.866 | A | 0.917 | A |
| Example 4 | | CC(C(OCCC)=O)(C)OC(C(C)C)=O | 0.874 | A | 0.919 | A |
| Example 5 | | CC(C(OC(C)C)=O)(C)OC(C(C)C)=O | 0.725 | A | 0.816 | A |
| Example 6 | | CC(C(OCCCC)=O)(C)OC(C(C)C)=O | 0.882 | A | 0.921 | A |
| Example 7 | | CC(C(OCC(C)C)=O)(C)OC(C(C)C)=O | 0.733 | A | 0.820 | A |
| Example 8 | | CC(C(OC(C)CC)=O)(C)OC(C(C)C)=O | 0.733 | A | 0.820 | A |
| Example 9 | | CC(C(OC(C)C(C)C)=O)(C)OC(C(C)C)=O | 0.591 | A | 0.646 | A |
| Example 10 | | CC(C(OC1CCCC1)=O)(C)OC(C(C)C)=O | 0.789 | A | 0.834 | A |
| Example 2 | | COC(C(C)(C)OC(C(C)(C)C)=O)=O | 0.936 | A | 0.924 | A |

TABLE 3-continued

| | Structural formula | SMILES | Biowin5 Degradation probability | Score | Biowin6 Degradation probability | Score |
|---|---|---|---|---|---|---|
| Example 11 | | CC(C(OCC)=O)(C)OC(C(C)(C)C)=O | 0.943 | A | 0.925 | A |
| Example 12 | | CC(C(OCCC)=O)(C)OC(C(C)(C)C)=O | 0.951 | A | 0.927 | A |
| Example 13 | | CC(C(OC(C)C)=O)(C)OC(C(C)(C)C)=O | 0.802 | A | 0.833 | A |
| Example 14 | | CC(C(OCCCC)=O(C)OC(C(C)(C)C)=O | 0.959 | A | 0.929 | A |
| Example 15 | | CC(C(OCC(C)C)=O)(C)OC(C(C)(C)C)=O | 0.810 | A | 0.836 | A |

TABLE 4

| | Structural formula | SMILES | Biowin5 Degradation probabilty | Score | Biowin6 Degradation probability | Score |
|---|---|---|---|---|---|---|
| Comparative Example 1 | (Menthol) | CC(C)C1CCC(C)CC1O | 0.455 | B | 0.331 | B |
| Comparative Example 2 | (Menthone) | CC(C)C1CCC(C)CC1=O | 0.406 | B | 0.335 | B |
| Comparative Example 3 | (Carvone) | C=C(C)C(C1)CC=C(C)C1=O | 0.454 | B | 0.375 | B |

TABLE 4-continued

| | Structural formula | SMILES | Biowin5 Degradation probabilty | Score | Biowin6 Degradation probability | Score |
|---|---|---|---|---|---|---|
| Comparative Example 4 | ((E)-alpha-damascone) | CC1(C)C(C(/C=C/C)=O)C(C)=CCC1 | 0.398 | B | 0.216 | B |
| Comparative Example 5 | ((E)-beta-damascenone) | CC1(C)C(C(/C=C/C)=O)C(C)C=CC1 | 0.378 | B | 0.213 | B |

Example 16: Woody-Type Fragrance Composition

A fragrance composition was prepared by adding 45.9 parts by mass of the ethyl α-isobutyryloxyisobutyrate obtained in Example 3 to 54.1 parts by mass of a fragrance composition having a composition shown in Table 5.

According to the aroma evaluation by perfumers, addition of the ethyl α-isobutyryloxyisobutyrate of Example 3 to the fragrance composition having the composition described in Table 5 added gorgeousness, emphasized floral sweetness, and provided integrity. As a result, provided was a fragrance composition of a gorgeous, elegant, floral, and woody aroma, to which a fresh mint-like green nuance, fruity rose-like floral, and bitter woodiness was imparted.

The aroma of this fragrance composition seems to be suitable for perfuming men's facial cleansing foam, after-shave lotion, hair mousse, and the like.

TABLE 5

| Blend ingredients | parts by mass |
|---|---|
| D-Limonene | 23.7 |
| Linalool | 15.3 |
| Decanal (2%) (C-10) | 2.5 |
| Lemon oil | 2.2 |
| Cyclopentadecanone (10%) | 2.1 |
| Ambroxide (5%) | 1.4 |
| Lavender oil | 1.3 |
| Oakmoss absolute (10%) | 1.3 |
| 10-Undecanal (2%) | 1.2 |
| Dimethol (50%) | 0.7 |
| Coumarin | 0.6 |
| Geranium oil (50%) | 0.5 |
| 4-Isopropylcyclohexanol (10%) | 0.5 |
| Styralyl acetate (10%) | 0.5 |
| Lilial (50%) | 0.4 |
| Total | 54.1 |

*Blend ingredients in parentheses in the table were used as a solution diluted with dipropylene glycol. The figures represents mass % of the fragrance included in the solution.

Example 17: Woody-Type Fragrance Composition

A fragrance composition was prepared by adding 25.0 parts by mass of the methyl α-isobutyryloxyisobutyrate obtained in Example 1 to 75.0 parts by mass of a fragrance composition having a composition shown in Table 6.

According to the aroma evaluation by perfumers, addition of the methyl α-isobutyryloxyisobutyrate of Example 1 to the fragrance composition having the composition described in Table 6 tightened up the scent, clarified the floral sweetness, and improved the integrity. As a result, provided was a fragrance composition having a refreshing, floral, and woody aroma, to which mint-like, patchouli-like, and vetiver-like smoky woodiness was imparted.

The aroma of this fragrance composition seems to be suitable for perfuming aftershave lotion, men's skin cream, soap, and the like.

TABLE 6

| Blend ingredients | parts by mass |
|---|---|
| D-Limonene | 33.2 |
| Linalool | 21.5 |
| Lemon oil | 3.0 |
| Cyclopentadecanone (10%) | 3.0 |
| Lavender oil | 1.9 |
| Ambroxide (5%) | 1.9 |
| Decanal (2%) (C-10) | 1.8 |
| Geranium oil (50%) | 1.7 |
| Dimethol (50%) | 1.7 |
| Lilial (50%) | 1.4 |
| Coumarin | 0.9 |
| Oakmoss absolute (10%) | 0.8 |
| 10-Undecanal (2%) | 0.8 |
| 4-Isopropylcyclohexanol (10%) | 0.7 |
| Styralyl acetate (10%) | 0.7 |
| Total | 75.0 |

*Blend ingredients in parentheses in the table were used as a solution diluted with dipropylene glycol. The figures represent mass % of the fragrance included in the solution.

Example 18: Woody-Type Fragrance Composition

A fragrance composition was prepared by adding 20.4 parts by mass of the methyl α-pivaloyloxyisobutyrate obtained in Example 2 to 79.6 parts by mass of a fragrance composition having a composition shown in Table 7.

According to the aroma evaluation by perfumers, addition of the methyl α-pivaloyloxyisobutyrate of Example 2 to the fragrance composition having the composition described in Table 7 emphasized spiciness and floralness and enhanced the width and intensity of the scent. As a result, provided was a fragrance composition having a calm, elegant, floral, and woody aroma, to which mint-like freshness, spiciness, and floral sweetness were imparted.

The aroma of this fragrance composition seems to be suitable for perfuming soap, men's hair dressing, aftershave lotion, and the like.

TABLE 7

| Blend ingredients | parts by mass |
| --- | --- |
| D-Limonene | 39.0 |
| Ambroxide (10%) | 17.6 |
| β-Damascone (10%) | 8.6 |
| Cyclopentadecanone (25%) | 7.2 |
| Geranium oil | 2.7 |
| Lemon oil | 1.9 |
| α-Ionone (10%) | 1.6 |
| Lavender oil | 0.9 |
| Total | 79.6 |

*Blend ingredients in parentheses in the table were used as a solution diluted with dipropylene glycol. The figures represent mass % of the fragrance included in the solution.

Example 19: White Floral-Type Fragrance Composition

A fragrance composition was prepared by adding 15.0 parts by mass of the n-propyl α-isobutyryloxyisobutyrate obtained in Example 4 to 85.0 parts by mass of a fragrance composition having a composition shown in Table 8.

According to the aroma evaluation by perfumers, addition of the n-propyl α-isobutyryloxyisobutyrate of Example 4 to the fragrance composition having the composition described in Table 8 emphasized a green and floral feeing, improved the integrity, and enhanced the intensity of the entire scent. As a result, provided was a fragrance composition having a fresh white floral aroma, to which mint-like briskness, soft spiciness, and floralness having a green feeling were imparted.

The aroma of this fragrance composition seems to be suitable for perfuming skin lotions, deodorant sprays, deodorant sheets, shampoos, and the like.

TABLE 8

| Blend ingredients | parts by mass |
| --- | --- |
| Hydroxycitronellal | 19.6 |
| Phenethyl alcohol | 16.7 |
| Hexyl salicylate | 16.1 |
| α, α-Dimethylbenzylcarbinol | 10.3 |
| 4-tert-Butylcyclohexyl acetate | 10.3 |
| α-Methyl-1,3-benzodioxole-5-propanal | 6.7 |
| α-Terpineol | 4.3 |
| Limonene | 1.0 |
| Total | 85.0 |

INDUSTRIAL APPLICABILITY

An isobutyric ester compounds having a butyryloxy group or a pivaloyloxy group at the α-position according to an embodiment of the present invention has an excellent aroma and is expected to be used itself as a fragrance. Additionally, use of the compound as a fragrance ingredient can provide a fragrance composition excellent in aroma properties. The composition, when blended in a variety of products, exhibits desired perfuming properties.

Furthermore, it was shown that the compounds obtained in Examples each have excellent biodegradability and a low impact on the environment and are suitable for use.

The invention claimed is:
1. A compound represented by Formula (1):

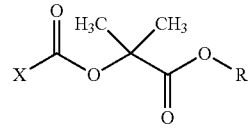

where X represents an isopropyl group or a t-butyl group, and R represents a linear, branched, or cyclic alkyl group having 1 to 5 carbon atoms;
provided that one where X is an isopropyl group and R is a t-butyl group is excluded.

2. The compound according to claim 1, wherein R is selected from the group consisting of a methyl group, an ethyl group, a n-propyl group, an isopropyl group, a n-butyl group, an isobutyl group, a sec-butyl group, a 3-methylbutan-2-yl group, and a cyclopentyl group.

3. The compound according to claim 1, wherein, in Formula (1), X is an isopropyl group.

4. The compound according to claim 1, wherein, in Formula (1), X is an isopropyl group, and R is a methyl group.

5. The compound according to claim 1, wherein, in Formula (1), X is an isopropyl group, and R is an ethyl group.

6. The compound according to claim 1, wherein, in Formula (1), X is an isopropyl group, and R is a n-propyl group.

7. The compound according to claim 1, wherein, in Formula (1), X is an isopropyl group, and R is an isopropyl group.

8. The compound according to claim 1, wherein, in Formula (1), X is an isopropyl group, and R is a n-butyl group.

9. The compound according to claim 1, wherein, in Formula (1), X is an isopropyl group, and R is an isobutyl group.

10. The compound according to claim 1, wherein, in Formula (1), X is an isopropyl group, and R is a sec-butyl group.

11. The compound according to claim 1, wherein, in Formula (1), X is an isopropyl group, and R is a 3-methylbutan-2-yl group.

12. The compound according to claim 1, wherein, in Formula (1), X is an isopropyl group, and R is a cyclopentyl group.

13. The compound according to claim 1, wherein, in Formula (1), X is a t-butyl group.

14. The compound according to claim 1, wherein, in Formula (1), X is a t-butyl group, and R is a methyl group.

15. The compound according to claim 1, wherein, in Formula (1), X is a t-butyl group, and R is an ethyl group.

16. The compound according to claim 1, wherein, in Formula (1), X is a t-butyl group, and R is a n-propyl group.

17. The compound according to claim 1, wherein, in Formula (1), X is a t-butyl group, and R is an isopropyl group.

18. The compound according to claim 1, wherein, in Formula (1), X is a t-butyl group, and R is a n-butyl group.

19. The compound according to claim 1, wherein, in Formula (1), X is a t-butyl group, and R is an isobutyl group.

20. A fragrance composition, comprising:
the compound of claim 1 as an active ingredient.

* * * * *